US007846131B2

(12) United States Patent  
Hudson et al.

(10) Patent No.: US 7,846,131 B2
(45) Date of Patent: Dec. 7, 2010

(54) ADMINISTRATION FEEDING SET AND FLOW CONTROL APPARATUS WITH SECURE LOADING FEATURES

(75) Inventors: Joseph A. Hudson, O'Fallon, MO (US); James Harr, Foristell, MO (US); Joel T. Wiesner, St. Peters, MO (US); Scott Kimsey, St. Peters, MO (US)

(73) Assignee: Covidien AG (CH)

( * ) Notice: Subject to any disclaimer, the term of this patent is extended or adjusted under 35 U.S.C. 154(b) by 1024 days.

(21) Appl. No.: 11/241,460

(22) Filed: Sep. 30, 2005

(65) Prior Publication Data

US 2007/0078431 A1 Apr. 5, 2007

(51) Int. Cl.
*A61M 1/00* (2006.01)

(52) U.S. Cl. .......................... 604/151; 604/30; 604/31; 604/32; 604/500; 251/95

(58) Field of Classification Search ................ 604/246, 604/248, 151, 131; 417/63; 251/213, 314, 251/339, 292, 291, 304, 310, 95, 96, 89
See application file for complete search history.

(56) References Cited

U.S. PATENT DOCUMENTS

| | | | |
|---|---|---|---|
| 2,483,924 A | 6/1946 | Moulinier | |
| 3,432,128 A | 3/1969 | Elleboudt | |
| 3,435,209 A | 3/1969 | Keahl | |
| 3,523,179 A | 8/1970 | Edwards et al. | |
| 3,673,476 A | 6/1972 | Hamburg | |
| 3,675,653 A | 7/1972 | Crowley et al. | |
| 3,693,025 A | 9/1972 | Brunton | |
| 3,851,976 A | 12/1974 | Meier | |
| 3,985,133 A | 10/1976 | Jenkins et al. | |

(Continued)

FOREIGN PATENT DOCUMENTS

DE    3627011 A1    2/1988

(Continued)

OTHER PUBLICATIONS

Garcia, et al: "Computational Prediction of PVC Degradation During Injection Molding in a Rectangular Channel", Polymer Engineering & Science, Jul. 2004, vol. 44, No. 7, pp. 1295-1312, Society of Plastics Engineers, United States.

(Continued)

*Primary Examiner*—Nicholas D Lucchesi
*Assistant Examiner*—Leah Stohr
(74) *Attorney, Agent, or Firm*—Edward S. Jarmolowicz, Esq.

(57) ABSTRACT

An administration feeding set for use with a flow control apparatus to deliver fluid from at least one fluid source to a patient. The feeding set includes tubing adapted to extend from the fluid source for flow of fluid through the tubing from the fluid source toward a patient. A locating finger projects outwardly from the tubing and is positioned on the tubing so that when received on the flow control apparatus in an operating position the finger permits a locating member of the flow control apparatus to close. However, when the tubing is received on the flow control apparatus in a non-operating position the finger does not permit the locating member to close thereby to verify whether the tubing is in the operating position on the flow control apparatus.

17 Claims, 16 Drawing Sheets

U.S. PATENT DOCUMENTS

| | | |
|---|---|---|
| 4,075,481 A | 2/1978 | Stoft et al. |
| 4,080,967 A | 3/1978 | O'Leary |
| 4,126,132 A | 11/1978 | Portner et al. |
| 4,300,048 A | 11/1981 | Barbier et al. |
| 4,346,296 A | 8/1982 | Passaro et al. |
| 4,424,011 A | 1/1984 | O'Brien et al. |
| 4,504,263 A | 3/1985 | Steuer et al. |
| 4,508,422 A | 4/1985 | Karlsson |
| 4,525,069 A | 6/1985 | Tanaka et al. |
| 4,537,561 A | 8/1985 | Xanthopoulos |
| 4,652,260 A | 3/1987 | Fenton, Jr. et al. |
| 4,665,391 A | 5/1987 | Spani |
| 4,714,463 A | 12/1987 | Archibald et al. |
| 4,763,032 A | 8/1988 | Bramm et al. |
| 4,792,424 A | 12/1988 | Loman |
| 4,845,487 A | 7/1989 | Frantz et al. |
| 4,845,489 A | 7/1989 | Hormel |
| 4,850,807 A | 7/1989 | Frantz |
| 4,878,896 A | 11/1989 | Garrison et al. |
| 4,882,575 A | 11/1989 | Kawahara |
| 4,884,013 A | 11/1989 | Jackson et al. |
| 4,884,103 A | 11/1989 | Yamada |
| 4,909,797 A | 3/1990 | Timothy |
| 4,913,703 A | 4/1990 | Pasqualucci et al. |
| 4,933,563 A | 6/1990 | Thus |
| 4,940,050 A | 7/1990 | Forssmann et al. |
| 4,944,748 A | 7/1990 | Bramm et al. |
| 4,945,244 A | 7/1990 | Castleman |
| 4,950,235 A | 8/1990 | Slate et al. |
| 4,958,910 A | 9/1990 | Taylor et al. |
| 4,976,590 A | 12/1990 | Baldwin |
| 5,057,081 A | 10/1991 | Sunderland |
| 5,078,741 A | 1/1992 | Bramm et al. |
| 5,158,437 A | 10/1992 | Natwick et al. |
| 5,181,842 A | 1/1993 | Sunderland et al. |
| 5,211,626 A | 5/1993 | Frank et al. |
| 5,237,309 A | 8/1993 | Frantz et al. |
| 5,237,450 A | 8/1993 | Strömberg |
| 5,250,027 A | 10/1993 | Lewis et al. |
| 5,256,155 A | 10/1993 | Yerlikaya et al. |
| 5,326,344 A | 7/1994 | Bramm et al. |
| 5,330,431 A | 7/1994 | Herskowitz |
| 5,336,174 A * | 8/1994 | Daoud et al. ............ 604/30 |
| 5,352,364 A | 10/1994 | Kruger et al. |
| 5,357,113 A | 10/1994 | Liston et al. |
| 5,364,364 A | 11/1994 | Kasvikis et al. |
| 5,415,641 A | 5/1995 | Yerlikaya et al. |
| 5,433,588 A | 7/1995 | Monk et al. |
| 5,433,704 A | 7/1995 | Ross et al. |
| 5,436,455 A | 7/1995 | Rosenthal et al. |
| 5,437,635 A | 8/1995 | Fields et al. |
| 5,502,111 A | 3/1996 | Huynh-Ba |
| 5,508,521 A | 4/1996 | Kraft et al. |
| 5,531,680 A | 7/1996 | Dumas et al. |
| 5,531,698 A | 7/1996 | Olsen |
| 5,536,935 A | 7/1996 | Klotzsch et al. |
| 5,560,355 A | 10/1996 | Merchant et al. |
| 5,567,120 A | 10/1996 | Hungerford et al. |
| 5,569,026 A | 10/1996 | Novak |
| 5,575,284 A | 11/1996 | Athan et al. |
| 5,584,811 A | 12/1996 | Ross et al. |
| 5,586,567 A | 12/1996 | Smith et al. |
| 5,602,664 A | 2/1997 | Doyle |
| 5,620,312 A | 4/1997 | Hyman et al. |
| 5,623,907 A | 4/1997 | Cotton et al. |
| 5,626,129 A | 5/1997 | Klimm et al. |
| 5,631,730 A | 5/1997 | Chupp et al. |
| 5,634,907 A | 6/1997 | Rani et al. |
| 5,649,810 A * | 7/1997 | Schweitzer et al. ......... 417/298 |
| 5,661,231 A | 8/1997 | Koskela |
| 5,681,284 A | 10/1997 | Herskowitz |
| 5,683,367 A | 11/1997 | Jordan et al. |
| 5,704,912 A | 1/1998 | Lawrence et al. |
| 5,711,654 A | 1/1998 | Afflerbaugh |
| 5,721,430 A | 2/1998 | Wong |
| 5,743,878 A | 4/1998 | Ross et al. |
| 5,752,813 A | 5/1998 | Tyner et al. |
| 5,767,976 A | 6/1998 | Ankerhold et al. |
| 5,788,674 A | 8/1998 | McWilliams |
| 5,798,699 A | 8/1998 | Bryant et al. |
| 5,818,049 A | 10/1998 | Bailey et al. |
| 5,828,458 A | 10/1998 | Taylor et al. |
| 5,851,631 A | 12/1998 | Borden et al. |
| 5,853,386 A | 12/1998 | Davis et al. |
| 5,903,006 A | 5/1999 | Kiuchi et al. |
| 5,920,018 A | 7/1999 | Wilkerson et al. |
| 5,961,450 A | 10/1999 | Merchant et al. |
| 6,011,985 A | 1/2000 | Athan et al. |
| 6,015,272 A | 1/2000 | Antaki et al. |
| 6,017,326 A | 1/2000 | Pasqualucci et al. |
| 6,023,970 A | 2/2000 | Blaine |
| 6,067,463 A | 5/2000 | Jeng et al. |
| 6,078,042 A | 6/2000 | Fellows |
| 6,095,986 A | 8/2000 | Braig et al. |
| 6,106,498 A | 8/2000 | Friedli et al. |
| 6,123,686 A | 9/2000 | Olsen et al. |
| 6,162,183 A | 12/2000 | Hoover |
| 6,219,138 B1 | 4/2001 | Swanson et al. |
| 6,227,817 B1 | 5/2001 | Paden |
| 6,234,992 B1 | 5/2001 | Haight et al. |
| 6,244,835 B1 | 6/2001 | Antaki et al. |
| 6,263,227 B1 | 7/2001 | Boggett et al. |
| 6,299,600 B1 | 10/2001 | Masaoka et al. |
| 6,325,422 B1 | 12/2001 | Verkaart et al. |
| 6,330,468 B1 | 12/2001 | Scharf |
| 6,344,030 B1 | 2/2002 | Duchon et al. |
| 6,370,408 B1 | 4/2002 | Merchant et al. |
| 6,390,590 B1 | 5/2002 | Hansburg |
| 6,402,717 B1 | 6/2002 | Reilly et al. |
| 6,437,316 B1 | 8/2002 | Colman et al. |
| 6,447,266 B2 | 9/2002 | Antaki et al. |
| 6,447,481 B1 | 9/2002 | Duchon et al. |
| 6,461,323 B2 | 10/2002 | Fowler et al. |
| 6,468,242 B1 | 10/2002 | Wilson et al. |
| 6,494,692 B1 | 12/2002 | Green |
| 6,496,711 B1 | 12/2002 | Athan et al. |
| 6,528,791 B1 | 3/2003 | Williams et al. |
| 6,626,862 B1 | 9/2003 | Duchon et al. |
| 6,635,033 B1 | 10/2003 | Hill et al. |
| 6,683,679 B2 | 1/2004 | Belenkii |
| 6,747,276 B2 | 6/2004 | Watanabe |
| 6,750,468 B2 | 6/2004 | Malmstrom et al. |
| 6,786,879 B1 | 9/2004 | Bolam et al. |
| 6,821,795 B2 | 11/2004 | Arno |
| 6,852,094 B2 | 2/2005 | Beck et al. |
| 6,863,658 B2 | 3/2005 | Hughett et al. |
| 6,890,291 B2 | 5/2005 | Robinson et al. |
| 6,891,343 B2 | 5/2005 | Petersen |
| 6,945,959 B2 | 9/2005 | Duchon et al. |
| 6,949,066 B2 | 9/2005 | Bearnson et al. |
| 6,958,053 B1 | 10/2005 | Reilly |
| 7,009,150 B2 | 3/2006 | Wennemann et al. |
| 7,018,363 B2 | 3/2006 | Cowan et al. |
| 7,025,716 B1 | 4/2006 | Meloul et al. |
| 7,026,773 B2 | 4/2006 | Petersen |
| 7,029,459 B2 | 4/2006 | Reilly |
| 7,041,082 B2 | 5/2006 | Blomquist et al. |
| 7,070,575 B2 | 7/2006 | Beck et al. |
| 7,092,796 B2 | 8/2006 | Vanderveen |
| 7,121,143 B2 | 10/2006 | Malmstrom et al. |
| 7,144,384 B2 | 12/2006 | Gorman et al. |
| 7,258,534 B2 | 8/2007 | Fathallah et al. |
| 2002/0030002 A1 | 3/2002 | Verkaart et al. |
| 2002/0036276 A1 | 3/2002 | Seeman |

| | | | | | | |
|---|---|---|---|---|---|---|
| 2004/0036273 | A1 | 2/2004 | McClary | EP | 0563351 B1 | 12/1997 |
| 2004/0097872 | A1 | 5/2004 | Delk et al. | EP | 0718006 B1 | 3/1999 |
| 2004/0158205 | A1 | 8/2004 | Savage | EP | 0891784 B1 | 9/2003 |
| 2005/0148938 | A1 | 7/2005 | Blomquist | EP | 0876825 B1 | 2/2005 |
| 2005/0186377 | A1 | 8/2005 | Hurst et al. | EP | 1829575 A1 | 9/2007 |
| 2005/0214131 | A1 | 9/2005 | Miles et al. | ES | 8500067 | 1/1985 |
| 2005/0267401 | A1 | 12/2005 | Price et al. | GB | 2065916 A | 7/1981 |
| 2005/0267418 | A1 | 12/2005 | Fournie et al. | JP | 2006233014 A | 9/2006 |
| 2005/0267439 | A1 | 12/2005 | Harr et al. | WO | 9320440 A1 | 10/1993 |
| 2006/0004327 | A1 | 1/2006 | Fournie et al. | WO | 9320441 A1 | 10/1993 |
| 2006/0007548 | A1 | 1/2006 | Watanabe | WO | 9508774 A2 | 3/1995 |
| 2006/0129104 | A1 | 6/2006 | Cowan et al. | WO | 9844320 A1 | 10/1998 |
| 2007/0208305 | A1 | 9/2007 | Wiesner et al. | WO | 9922783 A1 | 5/1999 |
| 2007/0253833 | A1 | 11/2007 | Hanlon et al. | WO | 2004028595 A1 | 4/2004 |
| | | | | WO | WO 2005/115501 A2 | 12/2005 |

FOREIGN PATENT DOCUMENTS

| | | | |
|---|---|---|---|
| DE | 3910250 | A1 | 10/1990 |
| EP | 0228217 | A1 | 7/1987 |
| EP | 0238809 | A2 | 9/1987 |
| EP | 0346548 | A1 | 12/1989 |
| EP | 0467805 | B1 | 3/1995 |

OTHER PUBLICATIONS

Compat Yset consisting of four photographs and description, publication date unknown but admitted as prior art, 5 pgs.

* cited by examiner

ADMINISTRATION FEEDING SET AND FLOW CONTROL APPARATUS WITH SECURE LOADING FEATURES

BACKGROUND

This invention relates generally to administration feeding sets to deliver fluids to patients by way of a flow control apparatus, and more particularly to a feeding set and pump having features for securely loading the feeding set on the pump.

Administering fluids containing medicine or nutrition to a patient is well known in the art. Typically, fluid is delivered to the patient by a pump set loaded on a flow control apparatus, such as a peristaltic pump, which delivers fluid to the patient at a controlled rate of delivery. A peristaltic pump usually comprises a housing that includes a rotor or the like operatively engaged to at least one motor through a gearbox. The rotor drives fluid through the tubing of the pump set by the peristaltic action effected by rotation of the rotor by the motor. The motor is operatively connected to a rotatable shaft that drives the rotor, which in turn progressively compresses the tubing and drives the fluid at a controlled rate through the pump set. The pump set may have a type of valve mechanism for permitting or preventing fluid flow communication through the pump set. A controller operates the motor or motors used to drive the rotor and, if necessary, control fluid flow as by operation of the valve mechanism.

In order for the pump to deliver an accurate amount of fluid corresponding with the flow parameters programmed into the pump, the administration feeding set must be correctly loaded on the pump. Typically, the valve mechanism of existing feeding sets must be seated on a shaft of the pump that controls the position of the valve mechanism and the amount of fluid flowing through the set. Existing feeding sets may be improperly installed or become dislodged such that the valve mechanism is not properly seated on the shaft or the tubing of the set is not engaged with the rotor. If the pump set is misaligned in the pump, the valve mechanism may not be operated and the pump may deliver an inaccurate amount of fluid to a patient or the pump generates a low flow alarm requiring the condition to be examined and the set reloaded.

SUMMARY OF INVENTION

In one aspect of the present invention, an administration feeding set for use with a flow control apparatus to deliver fluid from at least one fluid source to a patient comprises tubing adapted to extend from the at least one fluid source for flow of fluid through the tubing from the fluid source toward a patient. A locating finger projects outwardly from the tubing that is adapted to engage the flow control apparatus. The locating finger is positioned on the tubing so that when received on the flow control apparatus in an operating position the finger permits a locating member of the flow control apparatus to close, and when received on the flow control apparatus in a non-operating position the finger does not permit the locating member to close thereby to verify whether the tubing is in the operating position on the flow control apparatus.

In another aspect of the present invention, a flow control apparatus for use in delivering fluid to a patient through a fluid administration set comprises a housing including a receiving portion shaped to receive at least a portion of the administration set in an operating position and at least one other non-operating position. A pumping device is engageable with the administration set for driving flow of fluid within the administration set. A locating member is movable relative to the housing between a first position in which the locating member is spaced farther away from the receiving portion of the housing and a second position in which the locating member is closer to the receiving portion of the housing. The locating member is shaped for engaging the administration set in the non-operating position to inhibit movement of the locating member to the second position and for moving relative to the administration set in the operating position to the second position.

In another aspect, a method of loading an administration set into a flow control apparatus operable to act on the administration set for flowing fluid in the administration set to a patient comprises engaging at least a portion of the administration set in a receiving portion of a housing of the flow control apparatus. A locating member associated with the flow control apparatus is moved toward the receiving portion of the housing until the locating member reaches a closed position relative to the housing thereby indicating the administration set is in an operating position, or the locating member engages the administration set and is prevented from reaching the closed position. Whether the locating member is in the closed position indicates whether the administration set is in the operating position.

In still another aspect of the present invention, a flow control apparatus for use in delivering fluid to a patient through a fluid administration set generally comprises a housing including a receiving portion shaped to receive at least a portion of the administration set in an operating position and at least one other non-operating position. A pumping device is engageable with the administration set for driving flow of fluid within the administration set. A locating member is movable relative to the housing between a first position in which the locating member is spaced farther away from the receiving portion of the housing and a second position in which the locating member is closer to the receiving portion of the housing. The locating member is shaped for engaging the administration set in a position near the operating position to move the administration set to the operating position as the locating member moves from the first position to the second position.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
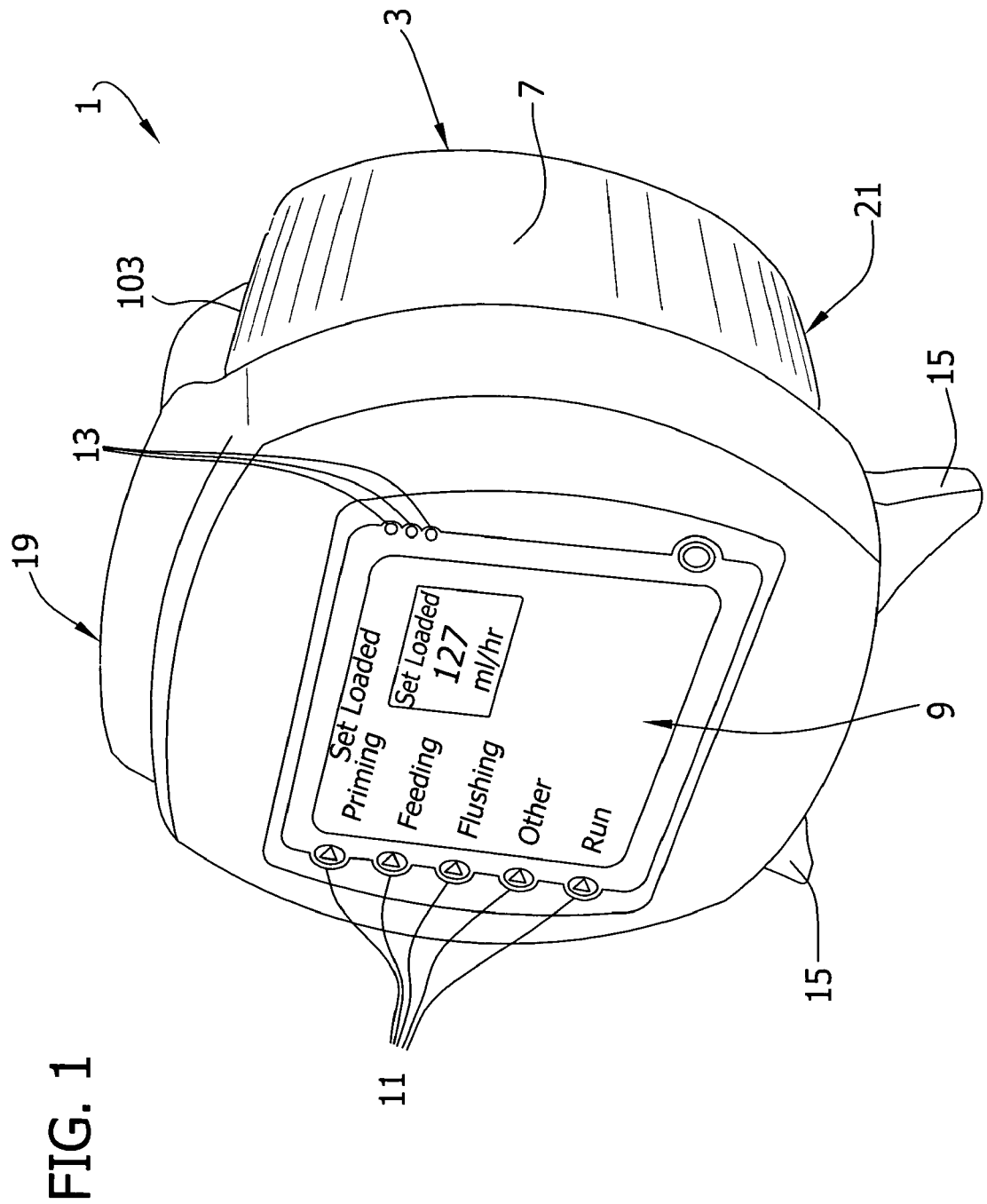
FIG. 1 is a perspective of an enteral feeding pump.
Figure 2:
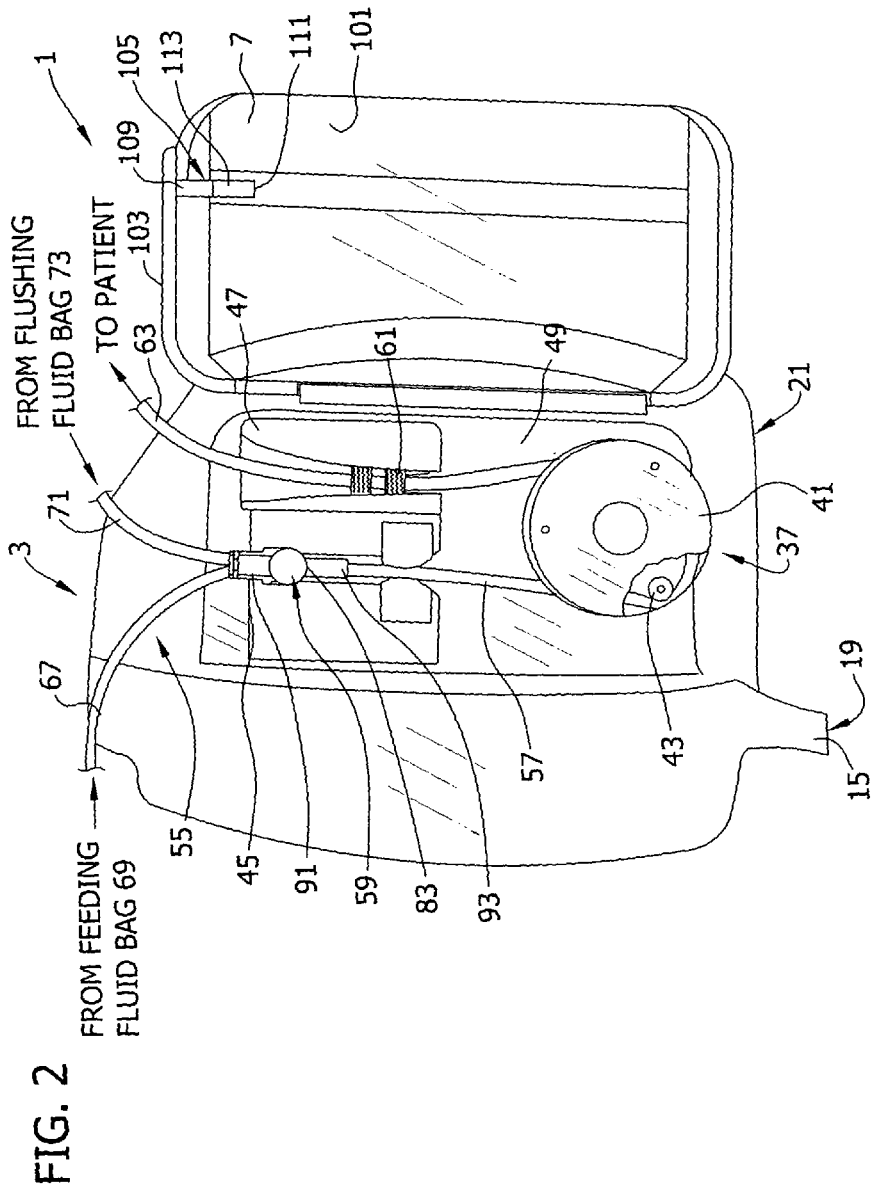
FIG. 2 is a side elevation thereof showing a fragmentary portion of an administration feeding set received in the pump.

Referring now to the drawings, an enteral feeding pump (broadly, "flow control apparatus") constructed according to the principles of the present invention is generally indicated at 1. The feeding pump comprises a housing generally indicated at 3 that is constructed so as to mount an administration feeding set (broadly, a "pump set") generally indicated at 5 (see FIGS. 2 and 5). The housing 3 includes a door 7 (broadly "closure") hinged to the remainder of the housing for swinging between a closed position (FIG. 1) and an open position (FIG. 2) which exposes a portion of the pump 1 that receives the administration feeding set 5. It will be appreciated that "housing" as used herein may include many forms of supporting structures (not shown), including without limitation multi-part structures and structures that do not enclose or house the working components of the pump 1. The pump 1 also has a display screen generally indicated at 9 on the front of the housing 3 that is capable of displaying information about the status and operation of the pump. Buttons 11 on the side of the display screen 9 are provided for use in controlling and obtaining information from the pump 1 and three light emitting diodes 13 also provide status information for the pump. Legs 15 at the bottom front of the housing 3 support the housing so that the display screen 9 is angled slightly upward for ease of viewing.

It will be understood that although the illustrated pump 1 is an enteral feeding pump, the present invention has application to other types of peristaltic pumps (not shown), including medical infusion pumps. The general construction and operation of the enteral feeding pump 1, except as set forth hereinafter, may be generally the same as disclosed in co-assigned U.S. patent application Ser. No. 10/853,958 filed May 24, 2004 and entitled ADMINISTRATION FEEDING SET AND VALVE MECHANISM, Ser. No. 10/854,136 filed May 24, 2004 and entitled FLOW CONTROL APPARATUS, and Ser. No. 10/853,926 filed May 25, 2004 entitled FLOW MONITORING SYSTEM FOR A FLOW CONTROL APPARATUS, the disclosures of which are incorporated by reference. Moreover, although an administration feeding set 5 is shown, other types of pump sets (not shown) can be used within the scope of the present invention.

Figure 3:
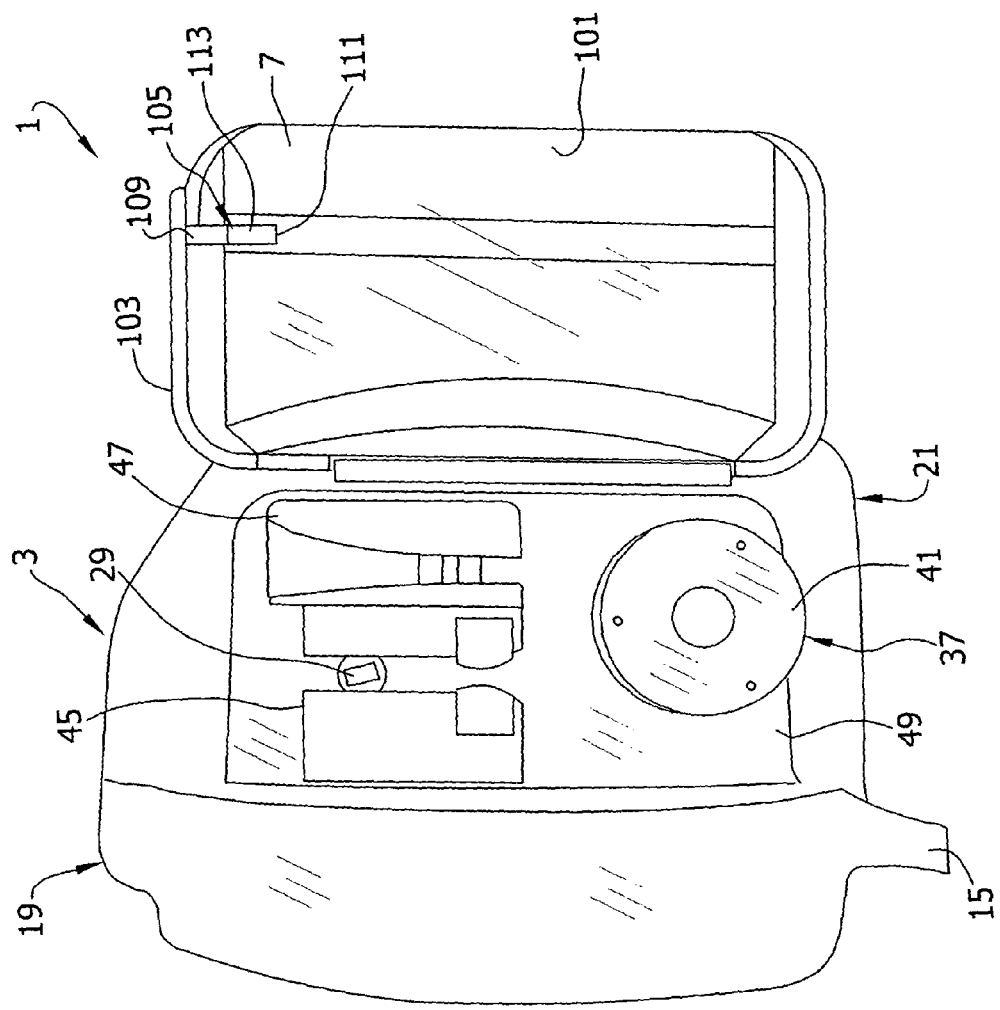
FIG. 3 is the side elevation of FIG. 2 with the administration feeding set removed.
Figure 4:
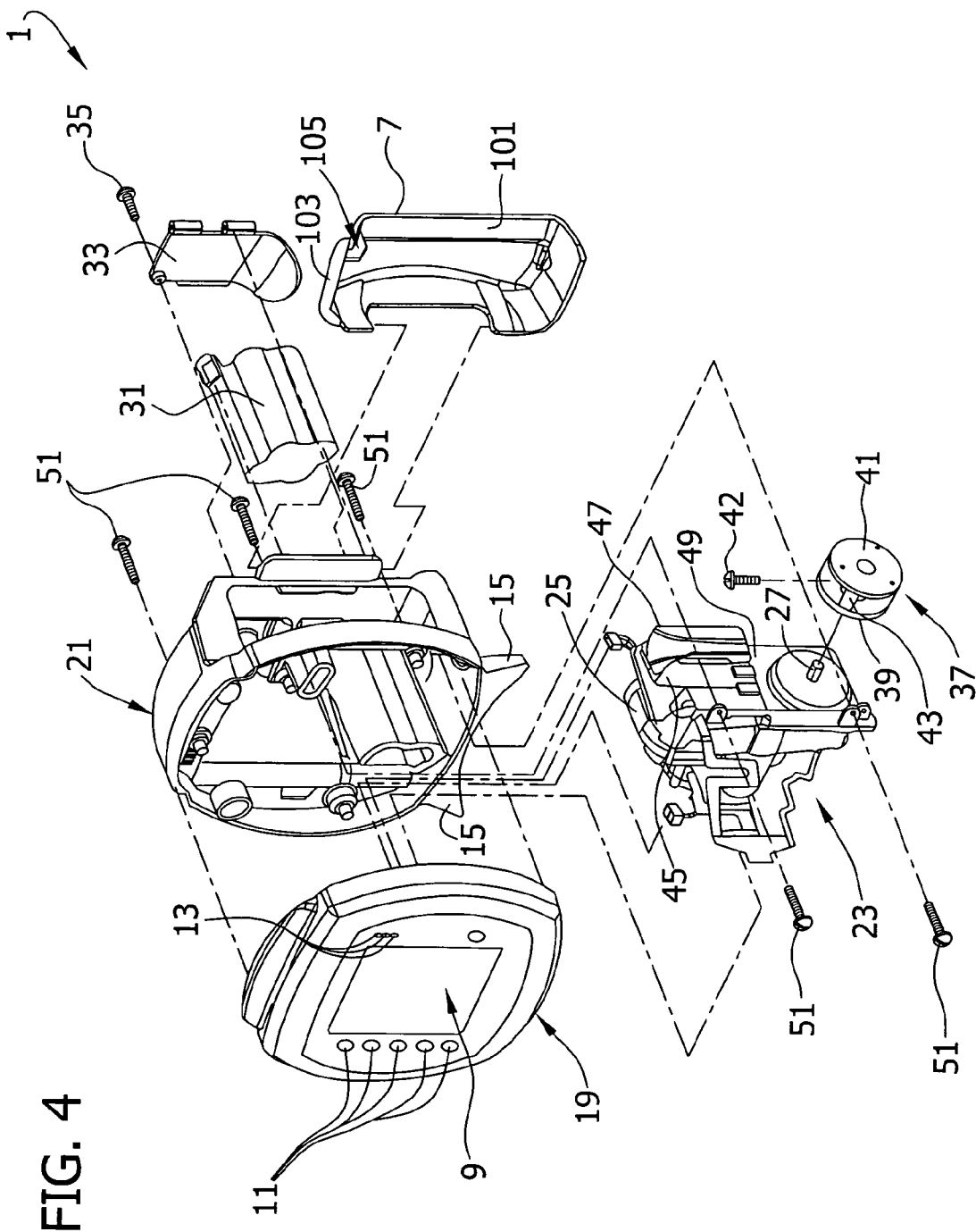
FIG. 4 is an exploded perspective of the pump.

Referring now also to FIG. 4, the display screen 9 is part of a front panel (generally indicated at 19) of the housing 3 removably attached to a main compartment (generally indicated at 21) of the housing that holds most of the operating components of the pump 1. The enteral feeding pump further includes a pumping unit (shown exploded from the main compartment and indicated generally at 23) comprising a pump motor 25 connected to a rotor shaft 27 and also to a valve shaft 29 (see, FIG. 3). It will be understood that the valve shaft 29 could be omitted, and/or that a separate motor (not shown) could be provided to operate the valve shaft within the scope of the present invention. A battery 31 may be received in the main compartment 21 of the housing 3 for powering the pump motor 25. A battery door 33 hingedly attached to the rear of the main compartment 21 closes the battery 31 within the compartment while providing access as needed. A bolt 35 holds the battery door 33 closed so that access to the battery 31 is normally blocked. Of course, a power source other than or in addition to a battery could be used.

A rotor (generally indicated at 37) is mounted on the rotor shaft 27 of the pumping unit 23 by a bolt 42. The rotor 37 includes an inner disk 39, an outer disk 41 and three rollers 43 (only one is shown) mounted between the inner and outer disks for rotation about their longitudinal axes relative to the disks. In the illustrated embodiment, the pump motor 25, rotor shaft 27 and rotor 37 may broadly be considered "a pumping device". The roller 43 engages the administration feeding set 5, which is also received in first and second chutes (designated 45 and 47, respectively) formed on a faceplate 49 of the pumping unit 23 on which the pump motor 25 is also mounted. The first and second chutes 45, 47 may broadly be considered "a receiving portion" of the housing that receive portions of the administration feeding set 5 in a manner that will be described in more detail hereinafter. The door 7 covers the chutes 45, 47 and rotor 37 when it is closed as it is in FIG. 1. Other bolts 51 hold various components of the pump 1 together.

Figure 5:
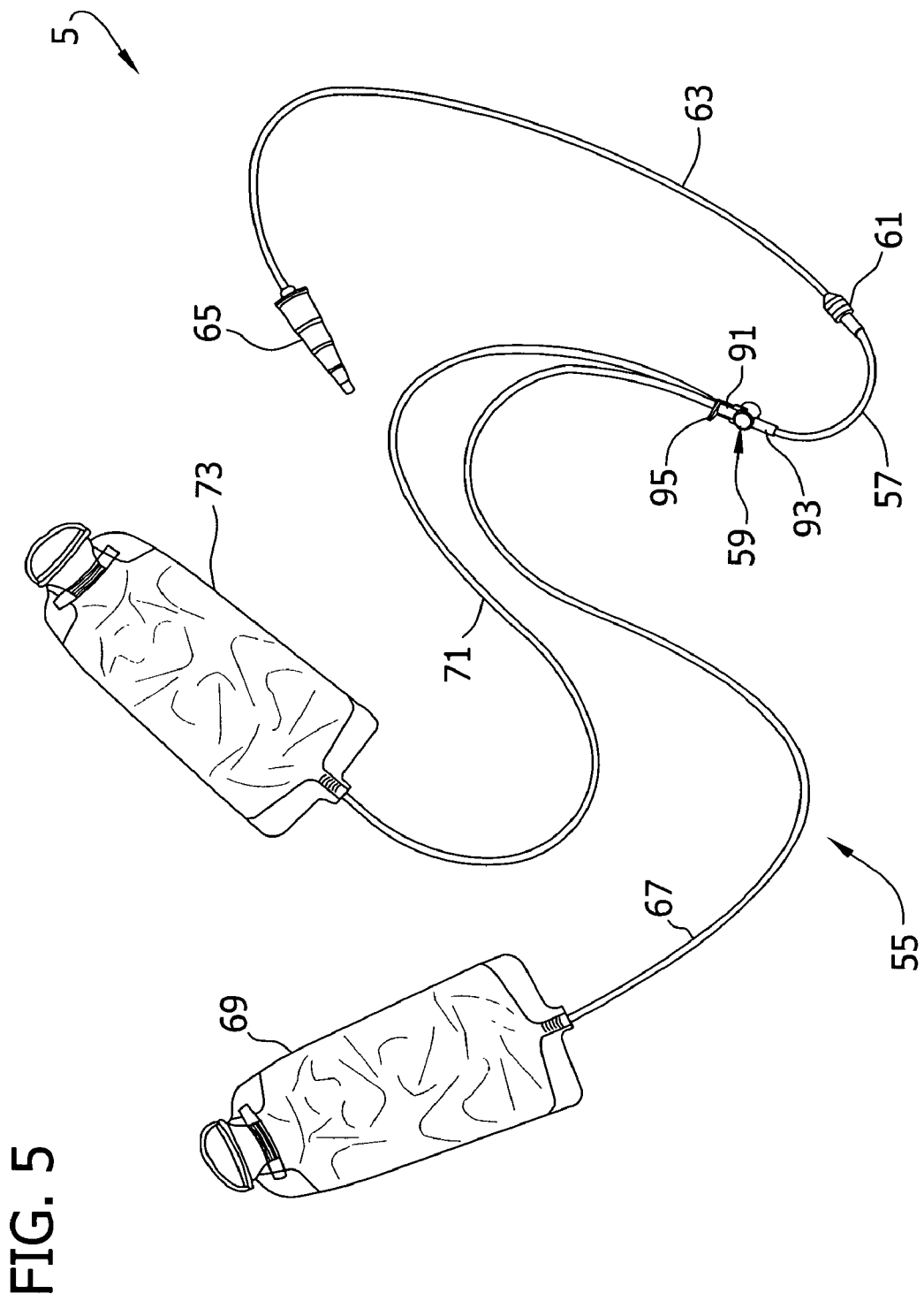
FIG. 5 is a perspective of the administration feeding set.

Referring now to FIG. 5, the administration feeding set 5 comprises tubing indicated generally at 55 that provides a fluid pathway between at least one source of fluid and a patient. Tubing 55 can be made of a medical grade, deformable silicone and comprises first tube section 57 connected between a valve mechanism, generally indicated at 59, and mounting member 61. A second tube section 63 is connected to the mounting member 61 and at an outlet of the tubing 55 to a connector, such as a barbed connector 65, suitable for connection to a gastrostomy device (not shown) attached to a patient. Third tube section 67 is connected at an inlet of the tubing 55 to a bag 69 of feeding fluid and to valve mechanism 59, and fourth tube section 71 is connected at an inlet of the tubing 55 to a bag 73 of flushing fluid and to the valve mechanism. The valve mechanism 59 is operable to selectively permit flow of feeding fluid from bag 69 or flushing fluid from bag 73, or prevent any fluid flow communication from the feeding or flushing fluid bags 69, 73 into the first tube section 57. The valve mechanism 59 can be turned to three positions. The first closes off all fluid flow from the third and fourth tube sections 67, 71 to the first and second tube sections 57, 63, the second allows feeding fluid to flow from the bag 69 to the first and second tube sections, and a third allows flushing fluid to flow from bag 73 to the first and second tube sections.

As previously stated, pump sets of different constructions may be used, for example a recertification set may be used to verify and/or correct the pump accuracy. The pump 1 can be configured to automatically recognize what kind of set is installed and to alter its operation to conform to that called for by the particular administration set. Still further, the pump 1 can be configured to detect with sensors whether the first tube section 57 is properly installed on the pump. Examples of suitable pump sets (including valve mechanisms) are shown in co-assigned U.S. Ser. No. 10/853,958 previously incorporated by reference.

Figure 7:
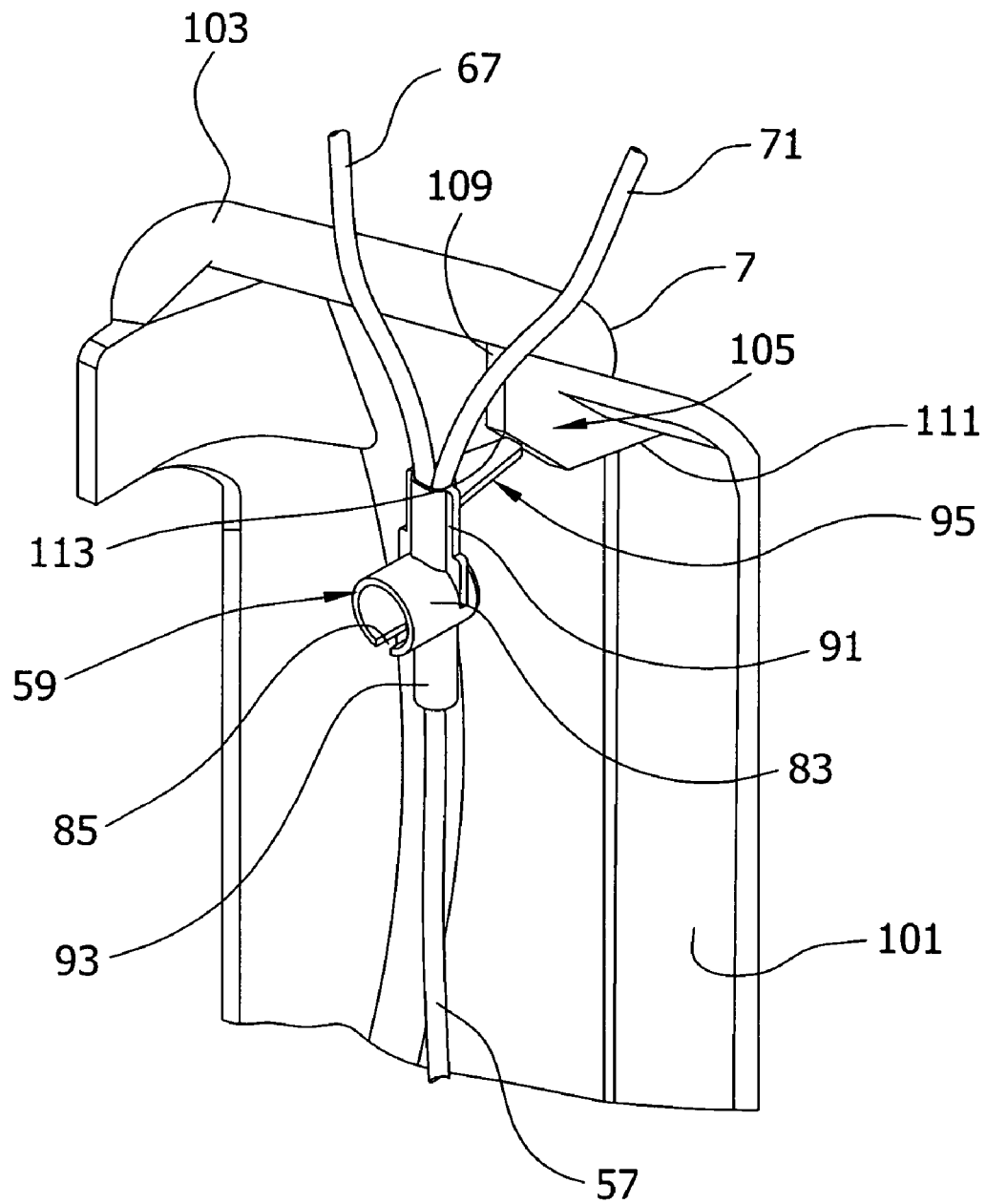
FIG. 7 is a fragmentary side perspective of a door of the feeding pump with the feeding set in a near-operating position.
Figure 7A:
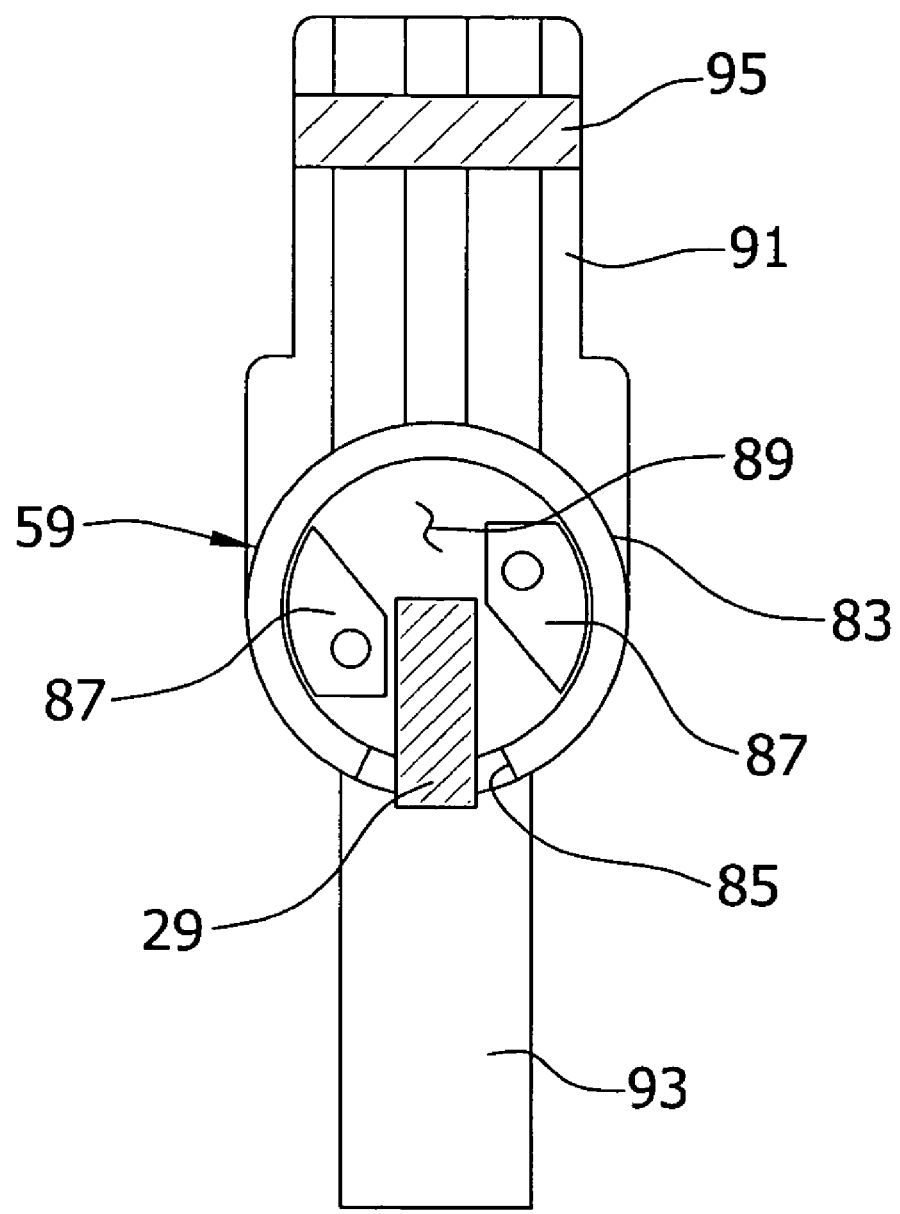
FIG. 7A is a schematic, fragmentary elevation of the feeding set and pump valve shaft with the feeding set in the near-operating position.
Figure 7B:
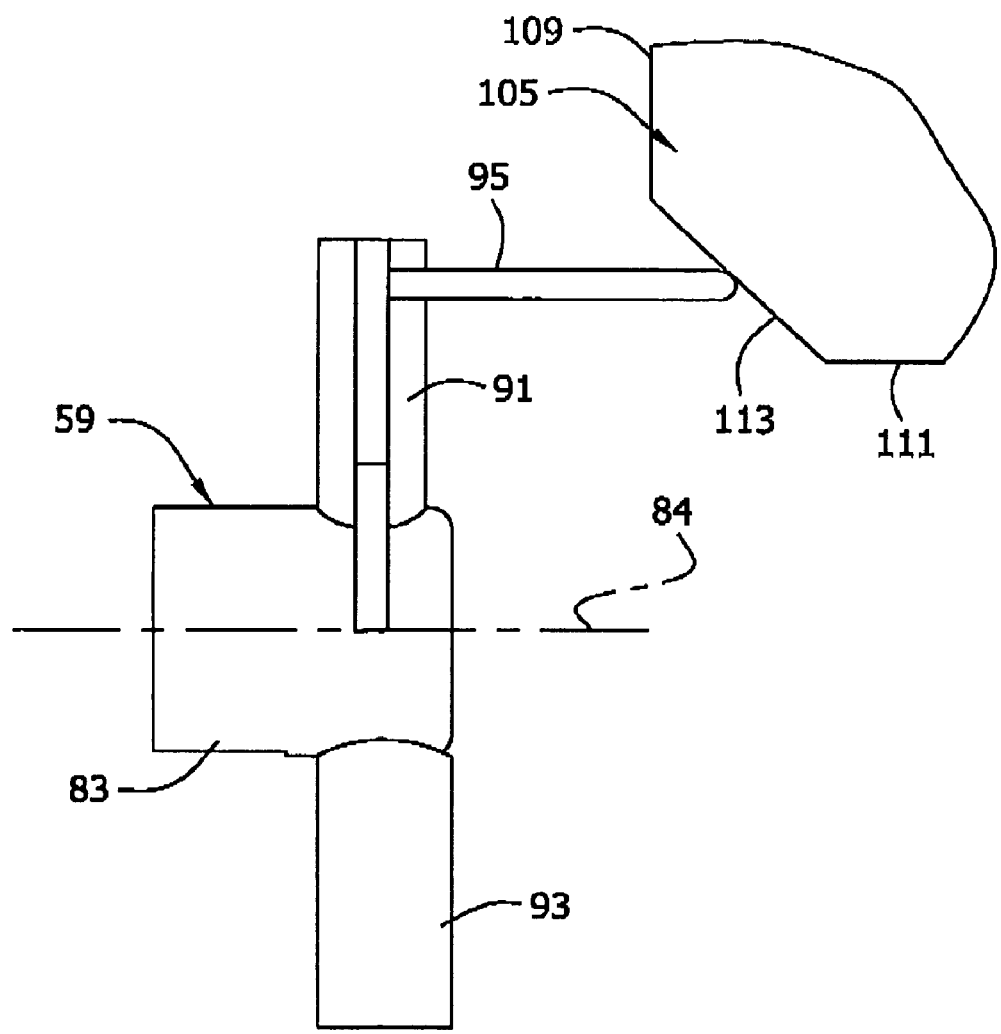
FIG. 7B is a schematic, fragmentary side elevation of the feeding set and a locating member of the door with the feeding set in the near-operating position.
Figure 8:
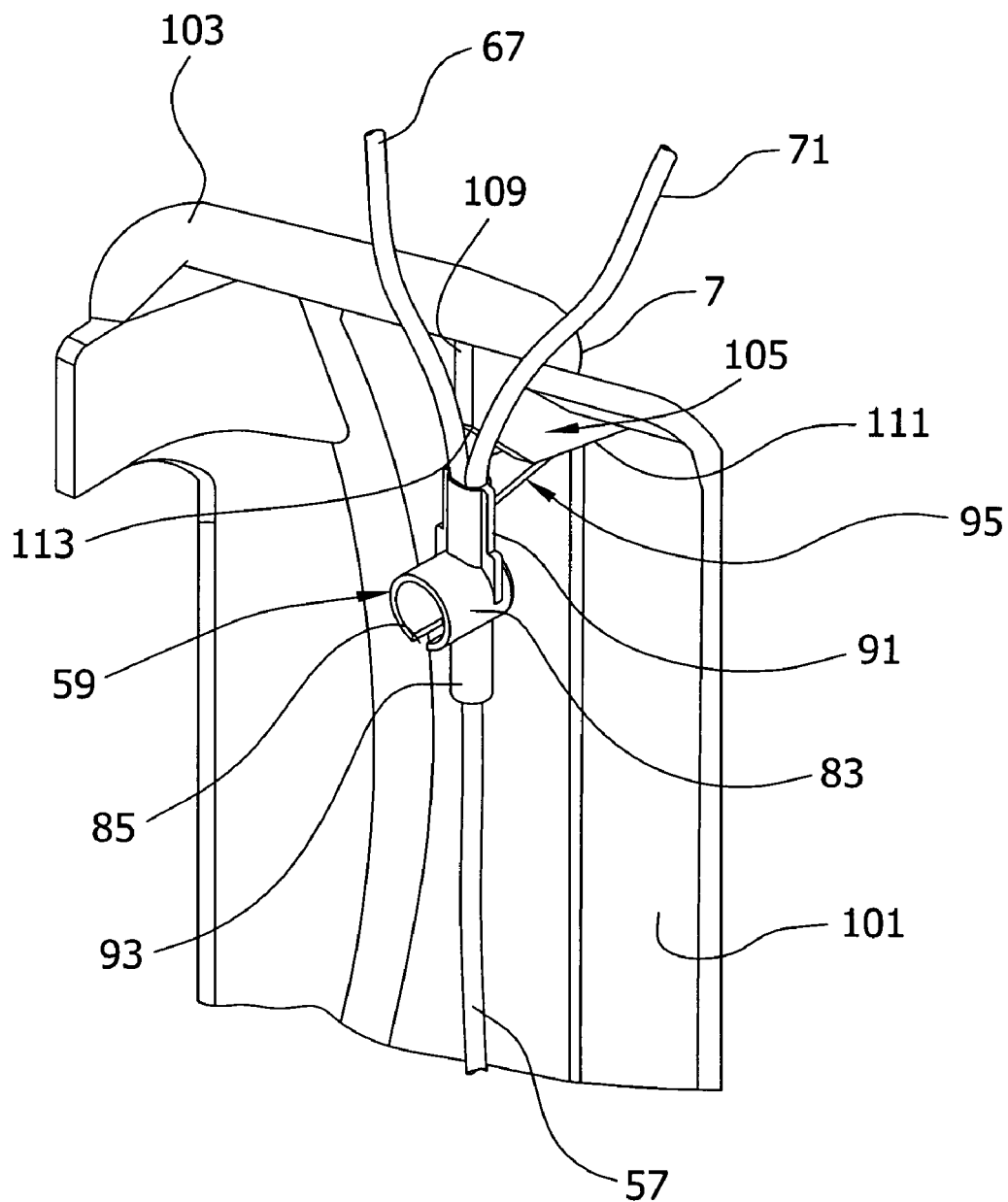
FIG. 8 is a schematic, fragmentary perspective of the door the feeding pump with the feeding set in an operating position.
Figure 8A:
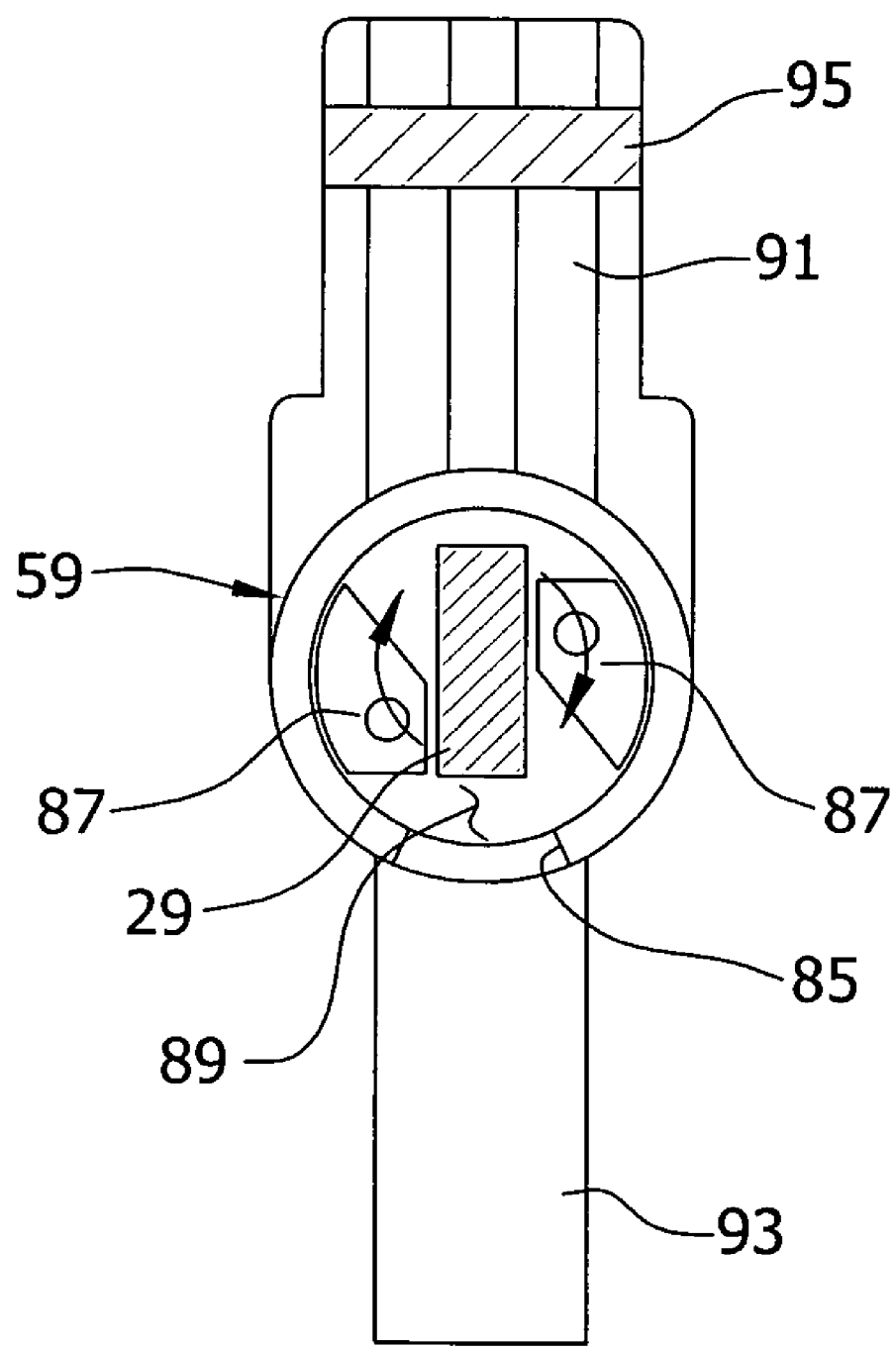
FIG. 8A is fragmentary elevation of the feeding set and pump valve shaft with the feeding set in the operating position.

Referring to FIGS. 7 7A and 7B, the valve mechanism 59 has a generally cylindrical valve body 83 having a longitudinal axis 84 and an opening 85 at the bottom of the valve body. The opening 85 is shaped to receive the valve shaft 29 when the valve mechanism 59 is loaded on the pump 1. The valve mechanism 59 includes a rotatable valve stem 87 in the body 83 that defines a channel 89 that is aligned with the opening 85 when the valve mechanism 59 is in the first (closed) position. When the feeding set 5 is in an operating position on the pump 1, the valve mechanism 59 is placed on the pump such that the valve shaft 29 is received in the channel 89 so that rotation of the valve shaft results in rotation of the valve mechanism (FIG. 8A). It is understood that the pump 1 sets the valve mechanism 59 to the first, second, or third position by rotating the valve shaft 29 based on the desired flow characteristics of the pump.

The feeding set 5 includes an upper sleeve 91 above the valve mechanism 59 that receives the third and fourth tube sections 67, 71 and a lower sleeve 93 below the valve mechanism that receives the first tube section 57. In the illustrated embodiment, a locating finger 95 projects outwardly from the upper sleeve 91. The finger 95 is elongate and projects radially outwardly from the tubing 55 at a location adjacent the valve mechanism 59 of the feeding set 5. The locating finger 95 is attached to the tubing 55 of the feeding set 5 such that vertical movement of the locating finger causes corresponding vertical movement of the valve body 83 of the valve mechanism 59. In the illustrated embodiment, the valve body 83, upper sleeve 91, lower sleeve 93, and locating finger 95 are formed as one piece but it is understood that the locating finger may be separate from the valve mechanism and attached to the feeding set 5 in a suitable manner.

As shown in FIG. 7, the door 7 has an inside surface 101, an upper surface 103, and a locating member, generally indicated at 105, positioned on the inside surface and projecting outwardly therefrom. The locating member 105 comprises a wedge-shaped formation near the upper surface 103 of the door. The locating member 105 has a first generally vertical surface 109, a second generally horizontal surface 111, and a third angled surface 113 between the first and second surface. The door 7 is mounted on the housing 3 for swinging movement between an open position (FIG. 2) allowing the feeding set 5 to be mounted on the pump 1 and a closed position (FIG. 1) covering the first and second chutes 45, 47. As discussed below in more detail, the locating member 105 is positioned on the door 7 to engage the locating finger 95 on the feeding set 5 when the door is moved from the open to the closed position to hold the feeding set 5 in an operating position of the valve mechanism 59.

Figure 8B:
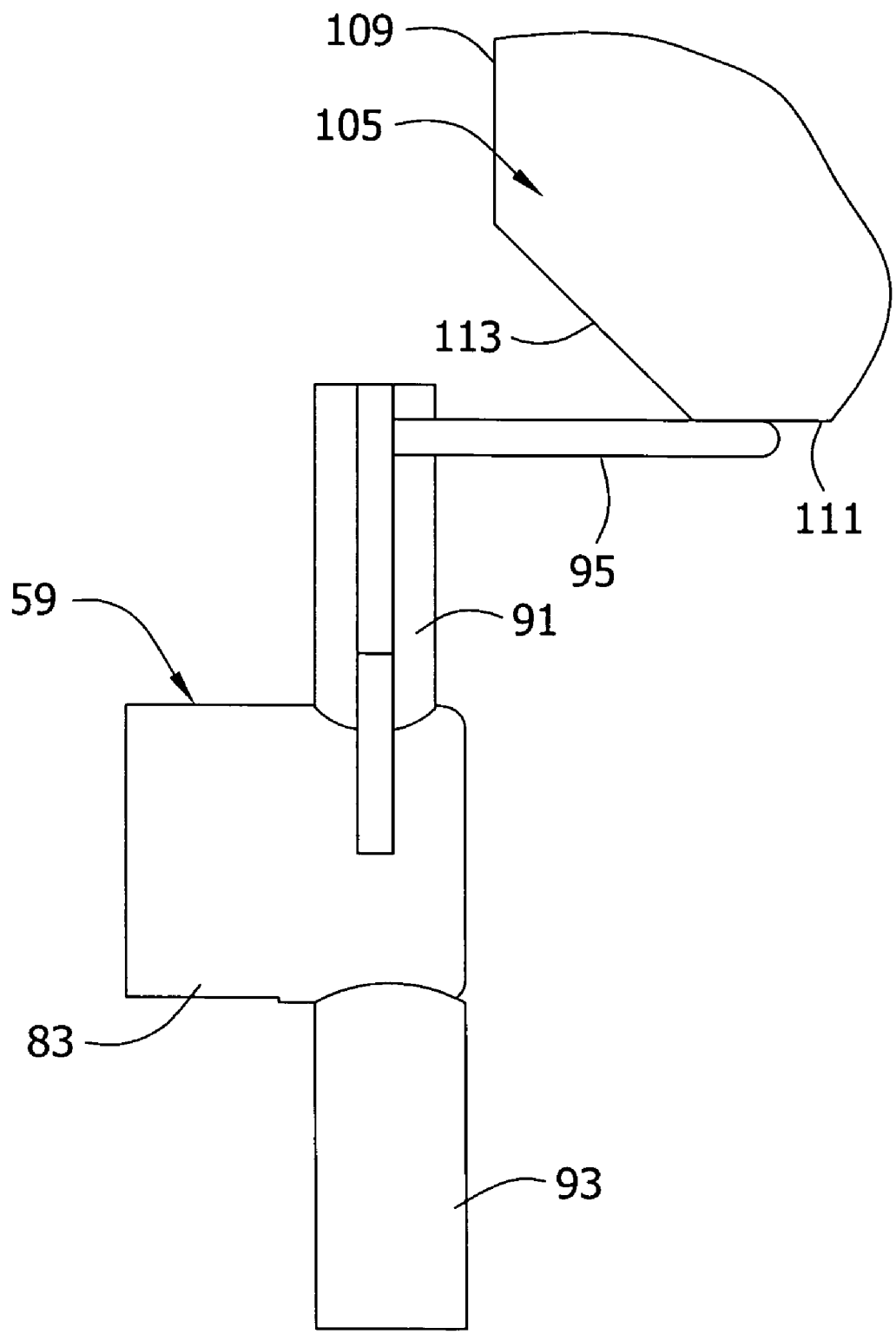
FIG. 8B is a schematic, fragmentary side elevation of the feeding set and the locating member of the door with the feeding set in the operating position.

In use, the administration feeding set feeding fluid bag 69 and flushing fluid bag 73 can be hung from a suitable support, such as an IV pole (not shown). The door 7 on the side of the pump 1 is swung open (as in FIG. 2) and the valve mechanism 59 can be placed in the first chute 45 in the operating position (FIGS. 8 and 8A) of the valve mechanism wherein the valve shaft 29 is received through the opening 85 into the body 83 and is engageable with valve stem 87 of the valve mechanism so that rotation of the valve shaft controls the position of the valve mechanism. The first tube section 57 is placed around the lower part of the rotor 37 and the mounting member 61 is placed in the second chute 47. The second chute is generally funnel-shaped so that the mounting member 61 can be placed into the chute 47 at a location in which the first tube section 57 is substantially stretched around the rotor 37. The first tube section 57 can relax slightly, pulling the mounting member 61 further down in the second chute 47. However, the first tube section 57 is maintained in a stretched condition around the rotor when properly installed on the pump 1. The door 7 can be re-closed to cover the first and second chutes 45, 47 and the rotor 37. When the door 7 is closed and the valve mechanism 59 has been properly loaded in the operating position, the horizontal surface 111 of the locating member 105 engages the locating finger 95 of the feeding set 5 to hold the feeding set in the operating position. As shown in FIG. 8B, the engagement of the locating member 105 with the locating finger prevents an upward pulling force on the feeding set 55 from dislodging the valve mechanism 59 from the operating position. The connector 65 at the end of the second tube section 63 can be connected to a conduit (not shown) attached to the patient in a known manner. It will be understood that any suitable connection to the patient for delivering the fluid may be used without departing from the scope of the present invention.

Figure 6:
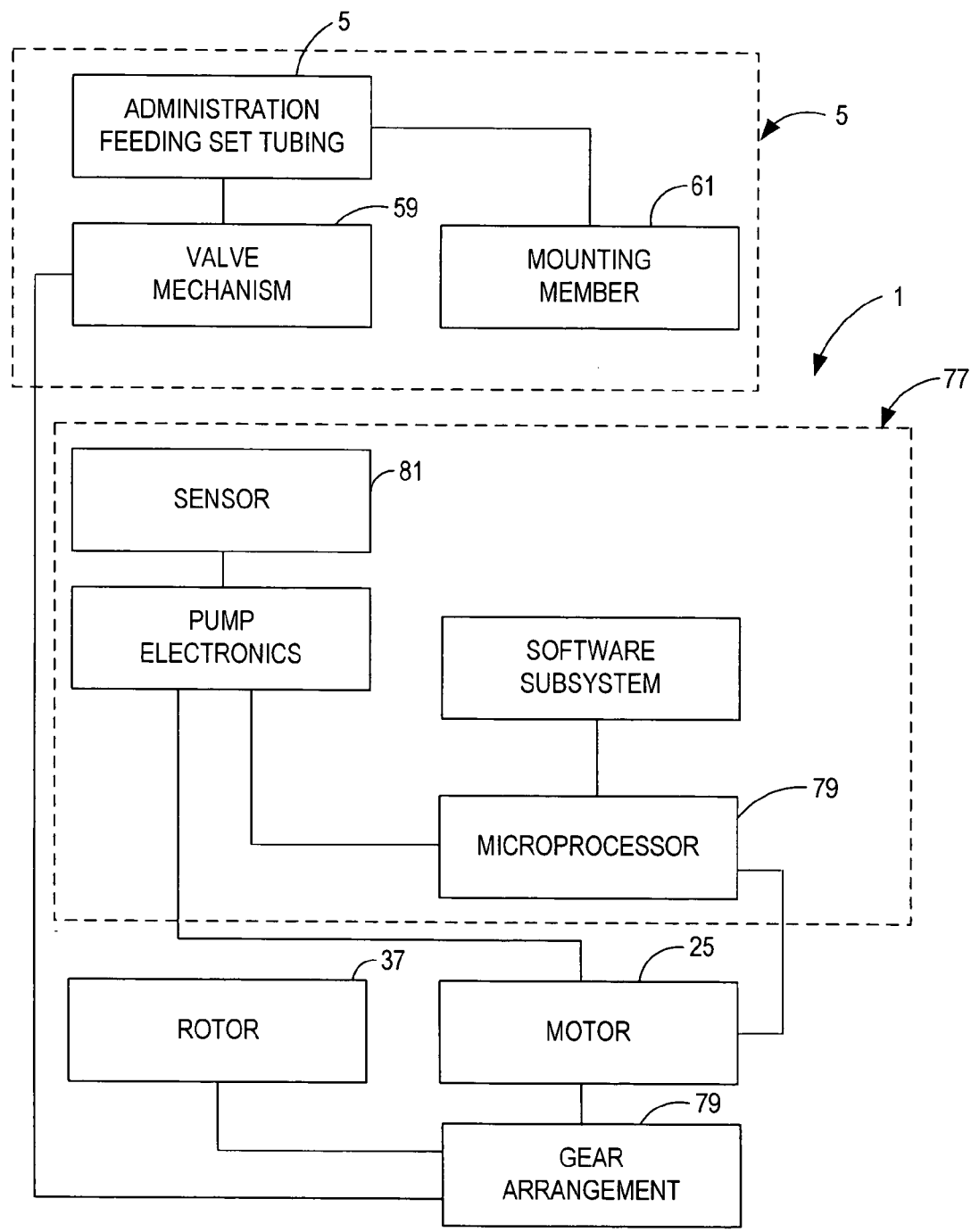
FIG. 6 a block diagram showing the elements of the pump.

The pump 1 can be programmed or otherwise controlled for operation in a desired manner. For instance, the pump 1 can begin operation to provide feeding fluids from bag 69 to the patient. The care giver may select (for example) the amount of fluid to be delivered, the rate at which the fluid is to be delivered and the frequency of fluid delivery. The pump 1 has a controller 77 (see, FIG. 6) including a microprocessor 79 that allows it to accept programming and/or to include pre-programmed operational routines that can be initiated by the care giver. The controller 77 is in communication with an administration set positioning sensor 81 that detects whether the administration feeding set 5 has been positioned properly, as previously described. Other sensors (not shown), such as a sensor that determines the type of administration set that has been placed in the pump 1 and a flow monitoring sensor can be in communication with the controller 77 to facilitate accurate operation of the pump. The controller 77 is also connected to the pump motor 25 for controlling its operation to actuate the valve mechanism 59 and the rotor 37. The pump motor 25 can operate the valve mechanism 59 and rotor 37 independently of each other.

FIGS. 7 and 7A show the valve mechanism 59 initially loaded in a near-operating position in which the valve body 83 is raised from the operating position a distance that is correctable by the engagement of the locating finger 95 with the locating member 105. In general, if the valve mechanism 59 is positioned close enough to the operating position that it can be moved by the locating member 105 (as will be described) to the operating position, it is considered to be in a "near-operating" position. In the near-operating position, the locating finger 95 of the feeding set 5 engages the angled surface 113 of the mounting member 105 when the door 7 is moved from the open position to the closed position. The engagement of the angled surface 113 with the locating finger 95 forces the valve member 59 downward to the operating position (FIGS. 7-7B) when the door is swung towards the fully closed position. The angled surface 113 of the locating member facilitates contact of the locating member 105 with the locating finger 95 at a first (open) position of the door and drives the locating finger and valve mechanism 59 downward as the door (and locating member) is swung to a second position closer to the housing than the first position. It will be understood that an angled or inclined surface could be part of the locating finger 95 instead of the locating member 105, or that both the locating finger and the locating member could be formed with angled surfaces without departing from the scope of this invention. At the fully closed position of the door 7, the horizontal surface 111 of the locating member 105 contacts the top surface of the locating finger 95 and holds the valve mechanism 59 in the operating position.

Figure 9:
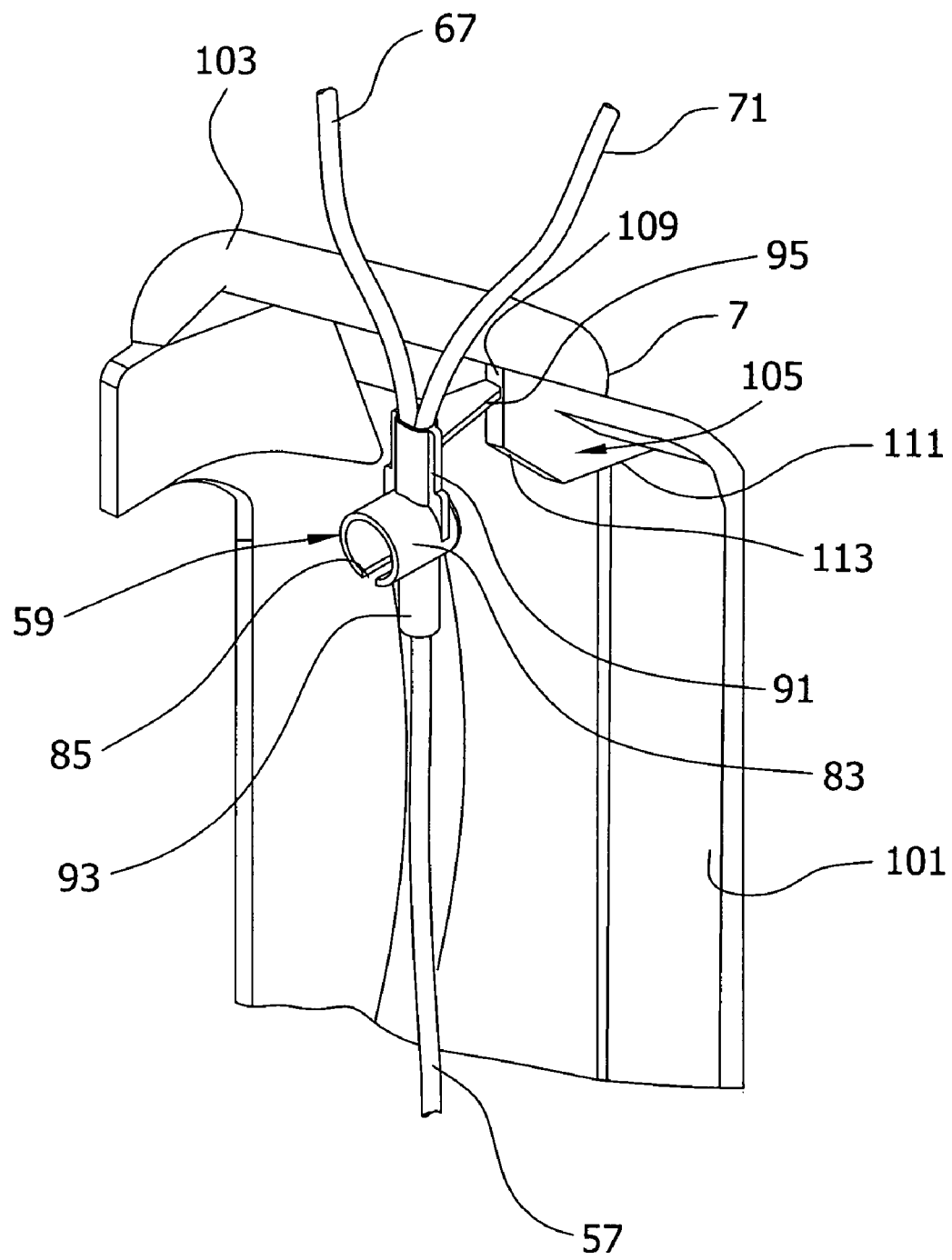
FIG. 9 is a schematic, fragmentary perspective of the door of the feeding pump with the feeding set in a non-operating position.
Figure 9A:
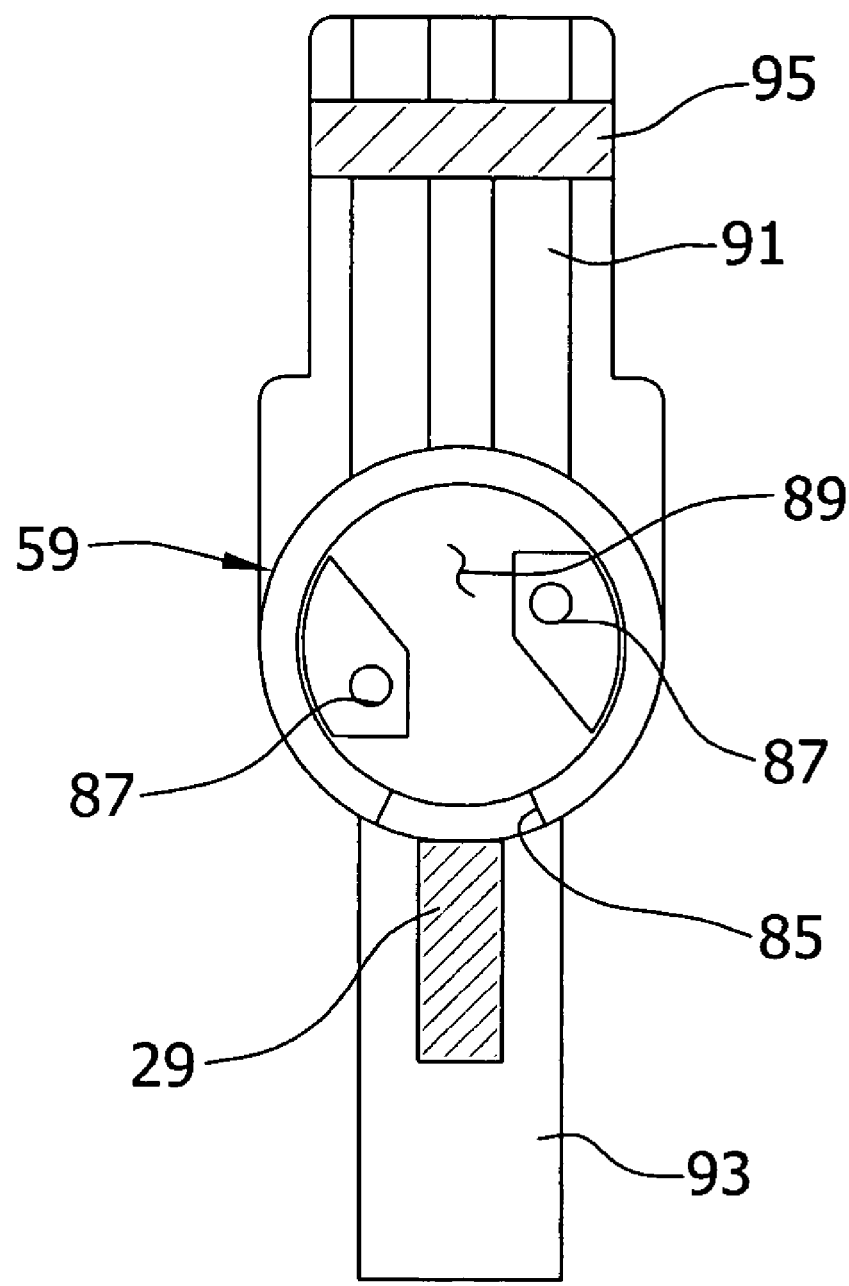
FIG. 9A is a fragmentary elevation of the feeding set and pump valve shaft with the feeding set in the non-operating position.
Figure 9B:
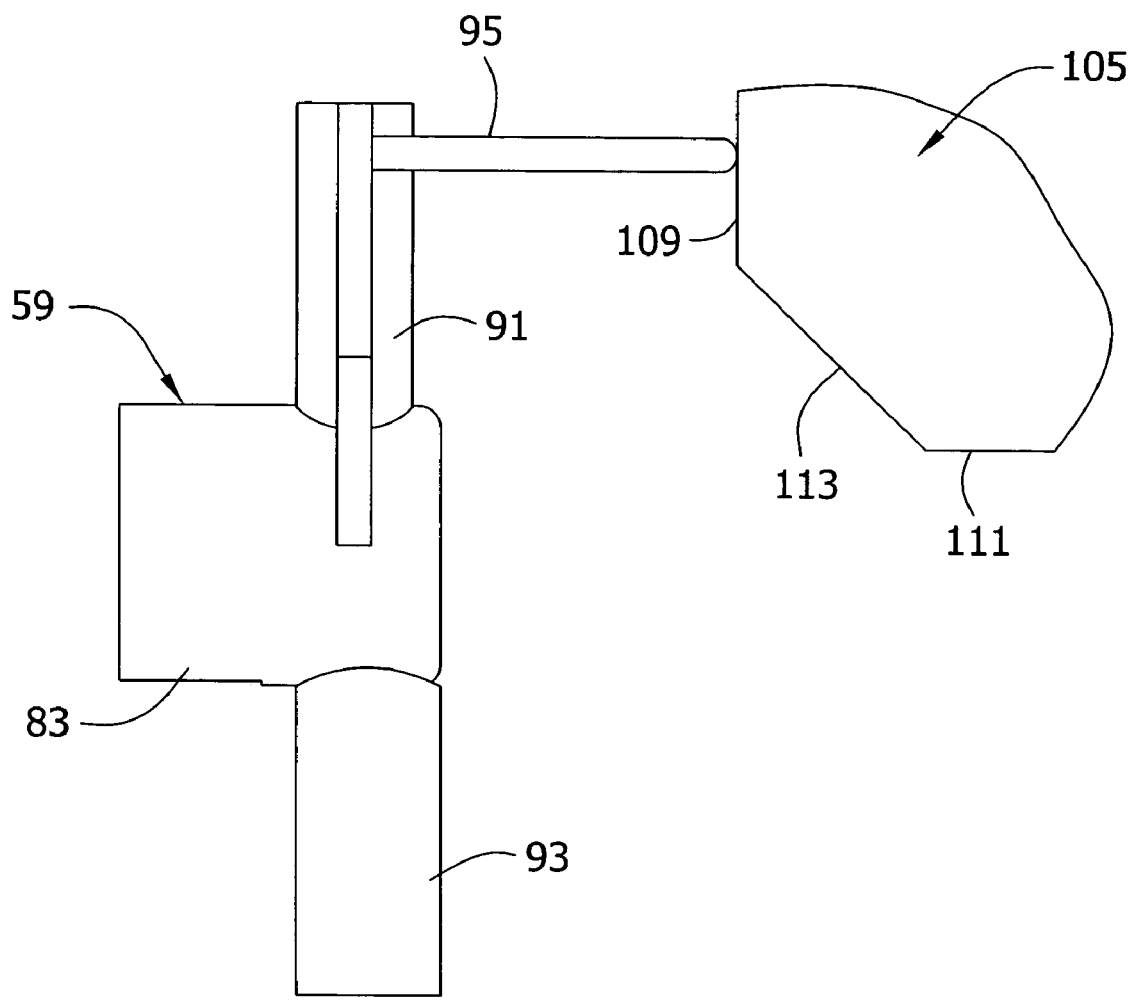
FIG. 9B is a schematic, fragmentary side elevation of the feeding set and the locating member of the door with the feeding set in the non-operating position.
Figure 10:
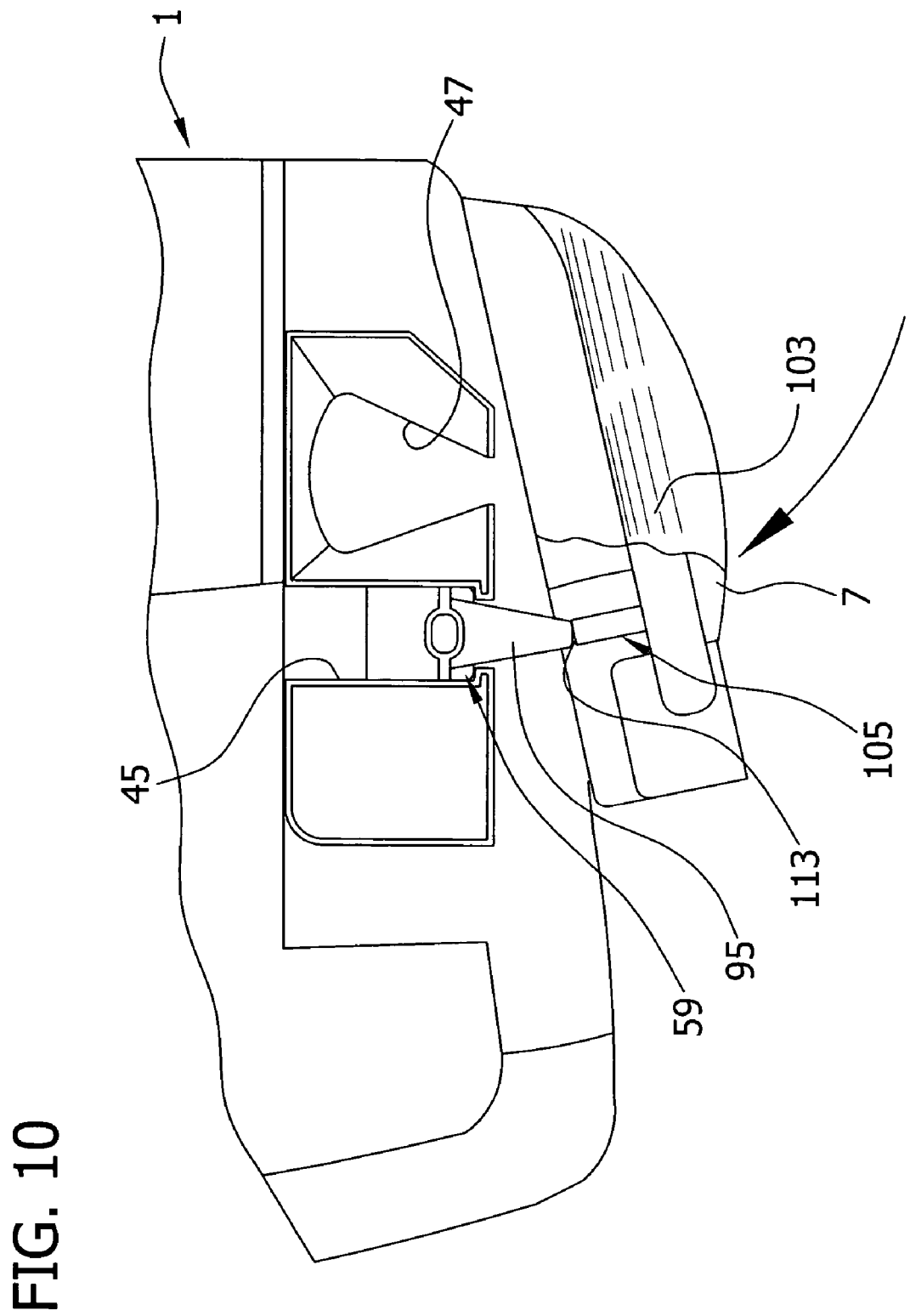
FIG. 10 is a fragmentary top plan view of the feeding pump with the feeding set in the non-operating position.

The valve mechanism 59 may be (inadvertently) loaded into the pump 1 in or be dislodged to assume a non-operating position (FIGS. 9, 9A, and 10) in which the valve body 83 is raised in the chute 47 such that shaft 29 is not fully received in the valve body or engaged with the valve stem 87 so that rotating of the shaft does not affect the position of the valve mechanism. The non-operating position of the valve mechanism 59 occurs when the feeding set 5 has been incorrectly loaded into the pump 1. As shown in FIGS. 9, 9A, and 10, if the valve mechanism 59 is raised from the operating position a sufficient amount, the locating finger 95 on the feeding set 5 will engage the vertical surface 109 of the locating member 105 when the door is moved from the open position to the closed position. The engagement of the locating finger 95 with the vertical surface 109 will prevent the door from fully closing and require the user to adjust the position of the feeding set 5 in the pump 1 prior to starting the pump. In this way, the engagement of the locating finger 95 on the feeding set 5 and the vertical surface 109 locating member 105 on the door 7 indicate whether the feeding set 5 is in the operating position on the pump.

A method of loading an administration set 5 into the pump 1 includes engaging at least a portion of the administration set 5 in the first and second chutes 45, 47. The locating member 105 on the door 7 is moved toward the first chute 45 until the locating member reaches a closed position relative to the housing thereby indicating the administration set is in an operating position or the locating member engages the locating finger 95 on the administration set and is prevented from reaching the closed position. Indication of whether the administration set 5 is in the operating position is given by whether the door can be moved to the closed position without interference of the locating member 105 with the locating finger 95. If the locating member 105 interferes with the locating finger 95 in a non-operating position of the administration feeding set, the door 7 will not be able to close and the user should adjust the position of the feeding set 5 to either the near-operating position (FIGS. 7 and 7A) or the operating position (FIGS. 8 and 8A) which allow the door of the pump 1 to close. If the administration feeding set 5 has been loaded in the near-operating position, the angled surface 113 of the locating member 105 will contact the locating finger 95 and drive the feeding set to the operating position when the door is moved from the open to the closed position. At the operating position, the valve mechanism 59 of the feeding set 5 will be in coupling engagement with the valve shaft 29 of the pump 1 and the horizontal surface 111 of the locating member 105 will be in engagement with the locating finger 95 to hold the valve mechanism in a secure stationary position.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. An administration feeding set for use with a flow control apparatus to deliver fluid from at least one fluid source to a patient, said flow control apparatus comprising a housing, a pumping unit in the housing comprising a rotatable valve shaft, and a closure on the housing movable between an open position and a closed position, the administration feeding set comprising:

tubing adapted to extend from said at least one fluid source for flow of fluid through the tubing from said fluid source toward a patient;

a valve mechanism in fluid communication with the tubing for controlling flow of fluid in the tubing, said valve mechanism comprising a valve body having a longitudinal axis and an open end;

a valve stem in the valve body rotatable relative to the valve body on said axis and accessible through the open end of the valve body for engagement with the valve shaft of the flow control apparatus;

an upper sleeve affixed to the valve body and extending up from an upper side of the valve body generally at right angles to said axis for connection to an upper section of said tubing;

a lower sleeve affixed to the valve body and extending down from a lower side of the valve body generally at right angles to said axis for connection to a lower section of said tubing;

a locating finger affixed to the upper sleeve and projecting laterally outwardly from the upper sleeve for engagement with a locating member on the closure of said flow control apparatus, the locating finger and open end of the valve body being located on opposite sides of the tubing for engagement of the valve stem with the valve shaft of the flow control apparatus and for engagement of the locating finger with the locating member on the closure, and the locating finger being positioned on the upper sleeve so that when the administration feeding set is received on the flow control apparatus in an operating position the finger permits the locating member of the flow control apparatus to close, and when administration feeding set is received on the flow control apparatus in a non-operating position the finger does not permit the locating member to close thereby to verify whether the administration feeding set is in the operating position on the flow control apparatus.

2. An administration feeding set as set forth in claim 1 wherein the locating finger projects radially outwardly from the upper sleeve and is not rotatable relative to the valve body.

3. An administration feeding set as set forth in claim 2 wherein the finger is elongate.

4. An administration feeding set as set forth in claim 1 wherein the finger and valve mechanism are located adjacent to each other for engagement with the flow control apparatus.

5. An administration feeding set as set forth in claim 4 wherein the finger and valve mechanism are positioned relative to each other so that upon engagement of the locating member of the flow control apparatus with the finger, the valve mechanism is forced by way of the finger and the tubing into the operating position on the flow control apparatus.

6. An administration feeding set as set forth in claim 4 wherein said valve mechanism is movable between at least two positions including an open position permitting fluid flow and a closed position preventing fluid flow.

7. An administration feeding set as set forth in claim 6 wherein said valve body has a periphery with an opening therein, and wherein said rotatable valve stem in the body defines a channel which is aligned with the opening in the closed position of the valve mechanism.

8. An administration feeding set as set forth in claim 1 in combination with the flow control apparatus.

9. An administration feeding set in combination with the flow control apparatus as set forth in claim 8 wherein the locating member comprises a locating formation engageable with the finger when the closure is moved to the closed position, the locating formation being shaped for moving the finger to bring the administration feeding set into the operating position.

10. An administration feeding set in combination with the flow control apparatus as set forth in claim 9 wherein at least one of the finger and the locating formation comprises a generally wedge-shaped structure.

11. An administration feeding set in combination with the flow control apparatus as set forth in claim 10 wherein the closure comprises a door cooperable with the housing to substantially enclose the locating finger and valve mechanism in the closed position.

12. A method of loading an administration set into a flow control apparatus operable to act on the administration set for flowing fluid in the administration set to a patient, the method comprising:

engaging at least a portion of the administration set in a receiving portion of a housing of the flow control apparatus;

moving the administration set in the receiving portion of the housing toward an operating position in which a valve mechanism of the administration set comprising a body having a longitudinal axis and an upper sleeve affixed to the body extending up from an upper side of the body generally at a right angle to said axis is in coupling engagement with a valve shaft in a housing of the flow control apparatus;

moving a closure of the flow control apparatus toward a closed position until a locating member on the closure reaches a closed position relative to the housing overlying a locating finger of the administration set thereby indicating the administration set is in said operating position, or the locating member engages the locating finger of the administration set and is prevented from reaching the closed position;

indicating as a result of whether the locating member is in the closed position whether the administration set is in the operating position;

wherein said locating finger is affixed to the upper sleeve and projects laterally outward from the upper sleeve for engagement with the locating member on the closure.

13. A method as set forth in claim 12 wherein moving the closure until the locating member reaches the closed position includes driving the administration set with the locating member toward the operating position.

14. A method as set forth in claim 13 wherein driving the administration set comprises engaging a wedge-shaped surface associated with one of the locating finger and the locating member with the other of the locating finger and the locating member as the locating member moves to the closed position.

15. A method as set forth in claim 13 wherein driving the administration set comprises moving the valve mechanism of the administration set into coupling engagement with the valve shaft of the flow control apparatus.

16. An administration feeding set as set forth in claim 1 wherein the tubing supports the locating finger.

17. A method as set forth in claim 12 wherein said valve mechanism comprises a valve body having an open end, and a rotatable valve stem in the valve body accessible through the open end of the valve body for engagement with the valve shaft of the flow control apparatus, and wherein the locating finger and open end of the valve body are located on opposite sides of the tubing for engagement of the valve stem with the valve shaft of the flow control apparatus and for engagement of the locating finger with the locating member on the closure.

* * * * *